(12) United States Patent
Pecherer et al.

(10) Patent No.: US 8,628,879 B2
(45) Date of Patent: Jan. 14, 2014

(54) MAGNETIC RESONANCE (MR) CONDITIONAL MEDICAL EQUIPMENT FOR USE IN MR ENVIRONMENTS

(75) Inventors: Eugeny Pecherer, Netanya (IL); Shiri Soffer, Tel Aviv (IL)

(73) Assignee: Truphatek International Ltd., Netanya South (IL)

( * ) Notice: Subject to any disclaimer, the term of this patent is extended or adjusted under 35 U.S.C. 154(b) by 1300 days.

(21) Appl. No.: 11/907,111

(22) Filed: Oct. 9, 2007

(65) Prior Publication Data
US 2008/0096099 A1 Apr. 24, 2008

Related U.S. Application Data

(60) Provisional application No. 60/828,700, filed on Oct. 9, 2006.

(51) Int. Cl.
*H01M 2/00* (2006.01)
*H01M 2/02* (2006.01)
*H01M 2/06* (2006.01)
*H01M 2/30* (2006.01)

(52) U.S. Cl.
USPC ............... 429/179; 429/1; 429/96; 429/170; 429/178

(58) Field of Classification Search
USPC ................................. 429/121–347
See application file for complete search history.

(56) References Cited

U.S. PATENT DOCUMENTS

| | | | |
|---|---|---|---|
| 3,220,888 A * | 11/1965 | Moore et al. | 429/1 |
| 5,169,733 A * | 12/1992 | Savovic et al. | 429/157 |
| 6,036,639 A | 3/2000 | Allred et al. | |
| 6,444,358 B1 | 9/2002 | Allred et al. | |
| 6,719,688 B2 | 4/2004 | Pecherer et al. | |

OTHER PUBLICATIONS

Rüsch Inc. "Care and Maintenance Instructions for Rüsch Laryngoscope Handles and Blades." 2001.*
Print out from website at www.minrad.com/devices/mr_inst.html, 2002.
U.S. Appl. No. 11/791,113, filed May 21, 2007, Pecherer.

* cited by examiner

*Primary Examiner* — Basia Ridley
*Assistant Examiner* — James Lee
(74) *Attorney, Agent, or Firm* — Novick, Kim & Lee, PLLC; Harold L. Novick

(57) ABSTRACT

Magnetic Resonance (MR) conditional medical equipment for use in MR environments. The MR conditional medical equipment includes MR conditional handheld battery operated devices, for example, laryngoscopes, flashlights, and the like, and MR conditional carbon zinc power packs for operating the devices. The devices can be designed to be inoperable by standard alkaline batteries which would render the medical equipment non MR conditional. Alternatively, the devices can have a sealed power pack compartment pre-installed with a non-replaceable carbon zinc power pack.

5 Claims, 4 Drawing Sheets

MAGNETIC RESONANCE (MR) CONDITIONAL MEDICAL EQUIPMENT FOR USE IN MR ENVIRONMENTS

CROSS-REFERENCE TO RELATED APPLICATIONS

This application claims priority on provisional application Ser. No. 60/828,700 filed on 9 Oct. 2006.

FIELD OF THE INVENTION

The present invention pertains to Magnetic Resonance (MR) conditional medical equipment for use in MR environments.

BACKGROUND OF THE INVENTION

Medical imaging modalities include Magnetic Resonance (MR) scanning. Medical equipment for use in MR environments is required to undergo specific MR testing, for example, ASTM standard F2052-6 entitled Standard Test Method for Measurement of Magnetically Induced Displacement Forces on Medical Devices in the Magnetic Resonance Environment to demonstrate compliance. MR conditional medical equipment includes inter alia handheld battery operated medical devices, for example, laryngoscopes, flashlights, and the like.

MR conditional laryngoscopes are commercially available from Minrad Inc., Buffalo, USA. On-line information regarding Minrad's MR tested laryngoscopes is available at http://www.minrad.com/devices/mr_inst.html. U.S. Pat. No. 6,036,639 to Allred, III et al. illustrates and describes a laryngoscope having low magnetic susceptibility suitable for use in MR environments. The laryngoscope is formed from MR conditional materials including non-metal materials and MR conditional metal materials including inter alia aluminum, heat treated austenitic stainless steel, bronze, brass, copper, and the like. U.S. Pat. No. 6,444,358 also to Allred, III et al. illustrates and describes a lithium battery having a low magnetic susceptibility suitable for use in MR environments. Minrad's MR conditional laryngoscopes have a unique terminal configuration for precluding operation with commercially available alkaline batteries which would render them non MR conditional. Minrad's lithium batteries are considerably more expensive than commercially available alkaline batteries.

SUMMARY OF THE INVENTION

The present invention is directed toward carbon zinc powered Magnetic Resonance (MR) conditional handheld battery operated devices including inter alia laryngoscopes, flashlights, and the like, for use in MR environments. Battery operated household items, for example, radios, calculators, flashlights, and the like, were traditionally powered by a single standard carbon zinc battery, two or more standard carbon zinc batteries either in a serial arrangement in the case of a need for a higher voltage or a parallel arrangement for providing a longer duration between battery replacements. For the purpose of the present invention, the term "standard carbon zinc batteries" implies carbon zinc batteries of a standard size, a standard voltage, and a standard terminal arrangement, for example, AAA size 1.5V carbon zinc batteries, AA size 1.5V carbon zinc batteries, C size 1.5V carbon zinc batteries, D size 1.5V carbon zinc batteries, and the like. Carbon zinc battery technology was the leading battery technology for many years but has now been largely superseded by alkaline battery technology due to advances in battery technology and manufacturing techniques. However, in contradistinction to the trend toward alkaline battery technology, carbon zinc batteries have an inherent low magnetic susceptibility comparable to lithium batteries thereby rendering them suitable for use in MR environments whilst being considerably less expensive than their lithium counterparts.

The present invention preferably proposes the use of standard carbon zinc batteries commercially available from, for example, Ningo Osel Battery Ltd, Ningbo, China (www.ningbobattery.com) for operating MR conditional medical devices thereby reducing their operating cost. However, since counterpart standard carbon zinc batteries and standard alkaline batteries, for example, an AA size 1.5V carbon zinc battery and an AA size 1.5V alkaline battery have identical size and terminal configurations, measures are required to prevent inadvertent use of alkaline batteries in intended MR conditional medical equipment which would render it non MR conditional. One approach envisaged by the present invention involves the provision of devices with power pack compartments and carbon zinc power packs having the same non-standard terminal configuration. One non-standard terminal configuration involves altering the location of preferably its negative terminal with respect to a standard battery. Another non-standard terminal configuration involves altering the dimensions of preferably its positive terminal with respect to a standard battery. Another approach envisaged by the present invention involves the provision of disposable devices having a sealed power pack compartment pre-installed with a non-replaceable carbon zinc power pack. Yet another approach envisaged by the present invention involves the provision of devices with power pack compartments and carbon zinc power packs having a non-standard mechanical configuration thereby precluding the inadvertent insertion of standard batteries.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DESCRIPTION OF THE PREFERRED EMBODIMENTS OF THE PRESENT INVENTION

MR Conditional Laryngoscopes

The present invention is described with reference to an ISO 7376/1 type laryngoscope including a handle and a detachable blade having a blade mounted light emitting element commercially available from, for example, the assignees of the present invention Truphatek International Ltd, Netanya, Israel (www.truphatek.com). In greater particularity, the present invention is described with reference to an ISO 7376/1 type laryngoscope as illustrated and described in commonly assigned U.S. Pat. No. 6,719,688 to Pecherer et al. The present invention is equally applicable to ISO 7376/3 type laryngoscopes including a handle with a handle mounted light emitting element and a detachable blade. The present invention is equally applicable to laryngoscopes including a handle with a permanently attached blade as illustrated and described in commonly assigned U.S. patent application Ser. No. 11/791,112. The light emitting elements can be bulbs, LEDs, and the like.

Figure 1:
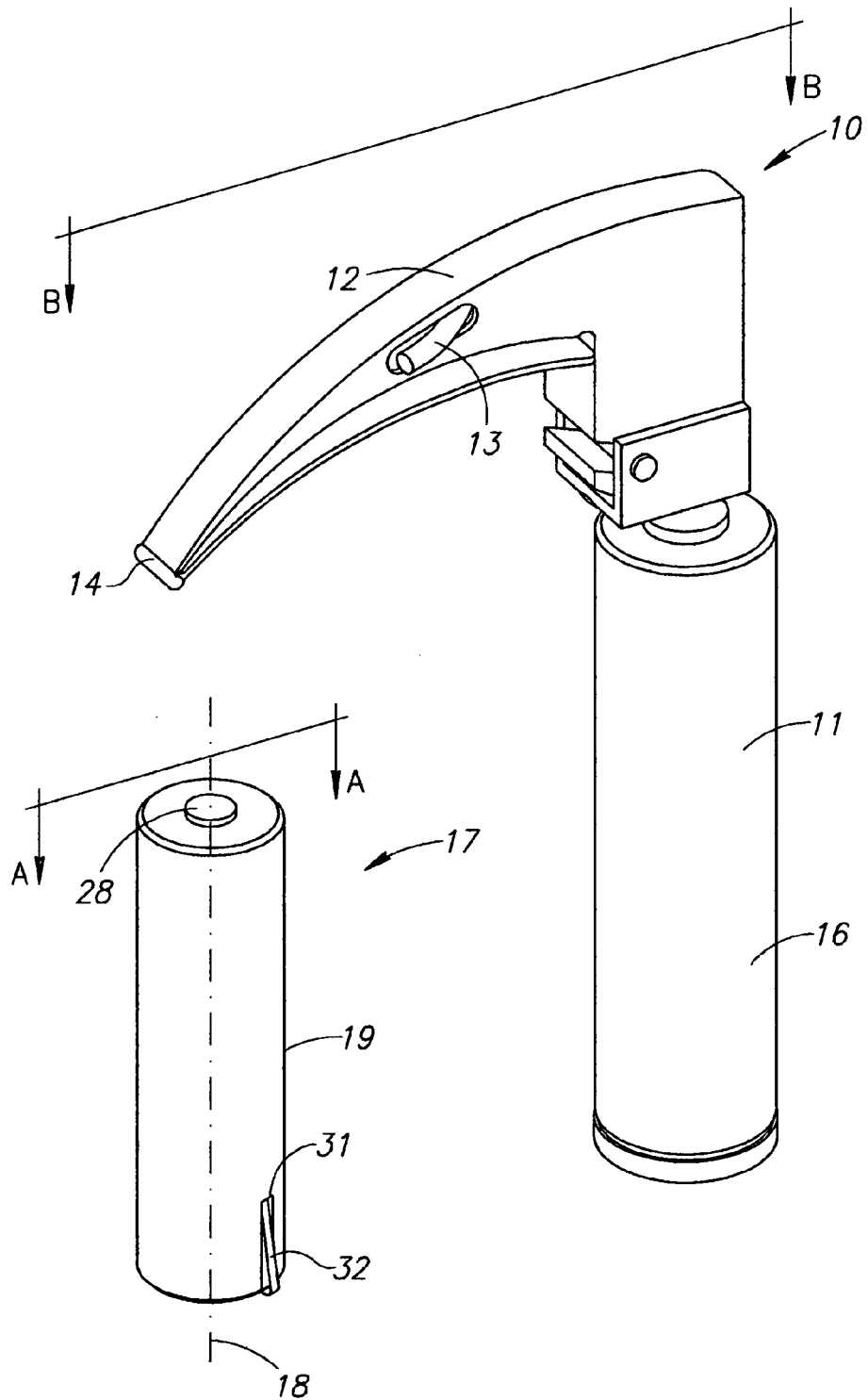
FIG. 1 is a pictorial view of a MR conditional laryngoscope and a carbon zinc power pack for operating same.
Figure 2:
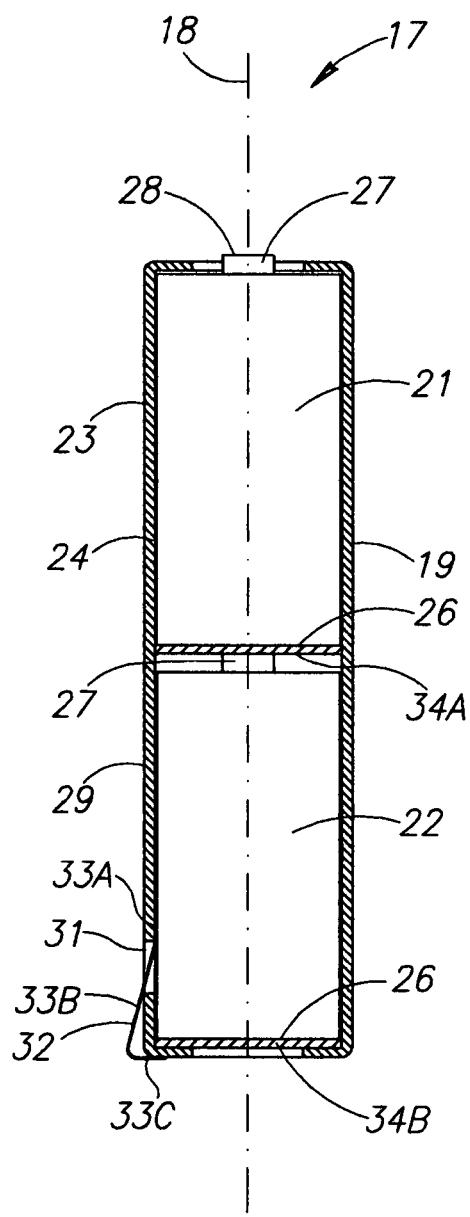
FIG. 2 is a longitudinal cross section of FIG. 1's carbon zinc power pack along line A-A therein.
Figure 3:
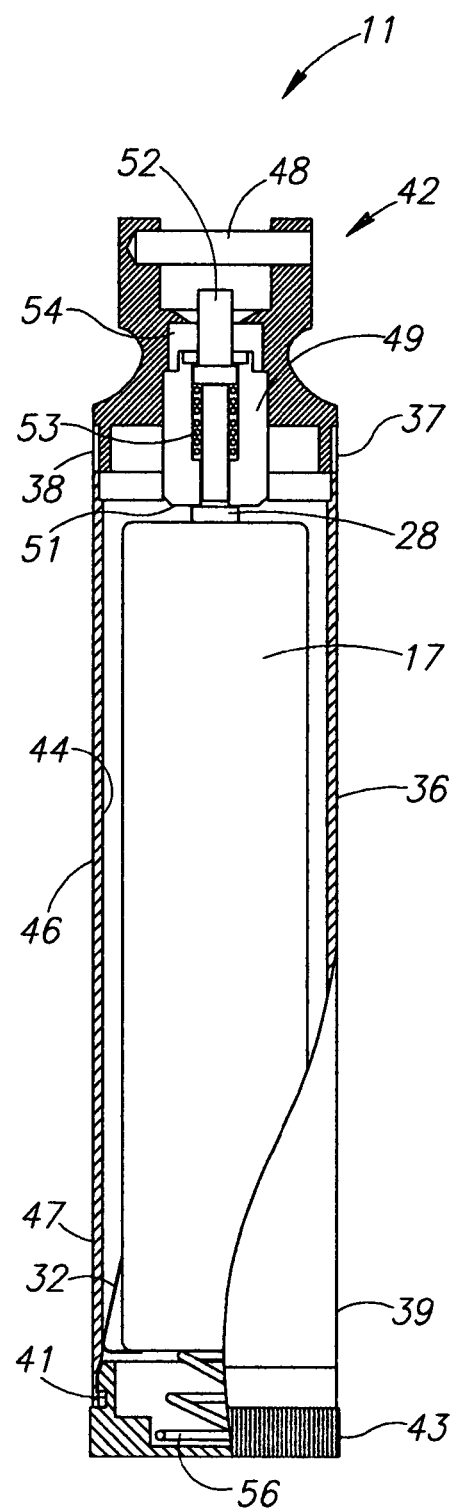
FIG. 3 is a longitudinal cross section of FIG. 1's laryngoscope's handle housing FIG. 1's carbon zinc power pack along line B-B in FIG. 1 in its Normally Open (NO) position.

FIGS. 1 to 3 show a MR conditional 7376/1 type laryngoscope 10 including an ISO 7376/1 type MR conditional handle 11 and a detachable ISO 7376/1 type MR conditional laryngoscope blade 12 with a light emitting unit 13 for providing illumination along the blade 12 towards its distal end 14 for illumination purposes during intubations. The handle 11 and the laryngoscope blade 12 are similar in construction and operation as their non MR conditional ISO 7376/1 type counterparts. The handle 11 has a power pack compartment 16 for snugly housing a replaceable MR conditional 3V carbon zinc power pack 17 for operating the laryngoscope 10. The power pack compartment 16 and the carbon zinc power pack 17 have a standard mechanical configuration and a non-standard terminal configuration. The laryngoscope blade 12 is preferably formed from either heat treated austenitic stainless steel or suitable rigid plastic material.

The carbon zinc power pack 17 has a longitudinal axis 18 and includes an electrically insulating casing 19 containing a leading standard 1.5V carbon zinc battery 21 and a trailing standard 1.5V carbon zinc battery 22 in series. The carbon zinc batteries 21 and 22 are typically either AA size or C size. The carbon zinc batteries 21 and 22 each include a negative zinc cup-shaped battery unit 23 with a cylindrical peripheral surface 24 and a circular bottom surface 26, and an electrically insulated copper positive terminal 27. The carbon zinc power pack 17 includes a positive terminal 28 constituted by the leading battery's positive terminal 27. The casing 19 includes a cylindrical peripheral surface 29 formed with an elongated axial directed aperture 31. The carbon zinc power pack 17 includes an axial directed negative terminal 32 affording the non-standard terminal configuration. The negative terminal 32 is in the form of an elongated copper member 33 configured to have one end 33A concealed under the electrically insulating casing 19 and in electrical contact with the trailing battery's battery unit 23, an intermediate section 33B extending through the axial directed aperture 31 and inclined with respect to the longitudinal axis 18, and a free end 33C spaced apart from the cylindrical peripheral surface 24 in a radial direction. The free end 33C is intended to be urged toward the longitudinal axis 18 on insertion of the carbon zinc power pack 17 in the laryngoscope's power pack compartment 16 for ensuring electrical contact. Alternatively, a power pack compartment 16 can be provided with a protrusion for ensuring electrical contact with the trailing battery's metal surface exposed through the elongated axial directed aperture 31. The carbon zinc power pack 17 preferably includes a leading circular copper plate 34A between the leading battery 21 and the trailing battery 22, and a trailing circular copper plate 34B adjacent the trailing battery's bottom surface 26 to prolong battery life.

The handle 12 includes a MR conditional cylindrical tube 36 with an upper end 37 having an upper internal screw thread 38, and a lower end 39 having a lower internal screw thread 41, a MR conditional ISO 7376/1 type head 42 for threading onto the screw thread 38, and a MR conditional cap 43 for threading onto the screw thread 41. The tube 36 is formed from aluminum and has an anodized internal and external surfaces 44 and 46 except for a small region 47 on its internal surface 44 contacted by the negative terminal 32 on installation of the carbon zinc power pack 17 into the handle 11. The head 42 includes a brass pivot pin 48 for detachable attachment of the laryngoscope blade 12, and a plastic tubular bushing 49 having a lowermost surface 51. The bushing 49 slidingly supports a brass pin 52 reciprocal between an uppermost position and a lowermost position for respectively breaking and making the electrical circuit for illumination purposes. The laryngoscope blade 12 depresses the brass pin 52 towards the positive terminal 28 for contacting same on snap fitting the laryngoscope blade 12 onto the handle 11 in its intubation ready state. The brass pin 52 is urged away from the positive terminal 28 to break electrical contact therewith by way of a bronze compression spring 53 and is stopped by a plastic stopper 54. The cap 43 is formed from anodized aluminum and includes an electrically insulated bronze compression spring 56 for positively bearing against the trailing battery's lowermost surface 26 for urging the positive terminal 28 against the bushing's lowermost surface 51.

MR Conditional Flashlights

Figure 4:
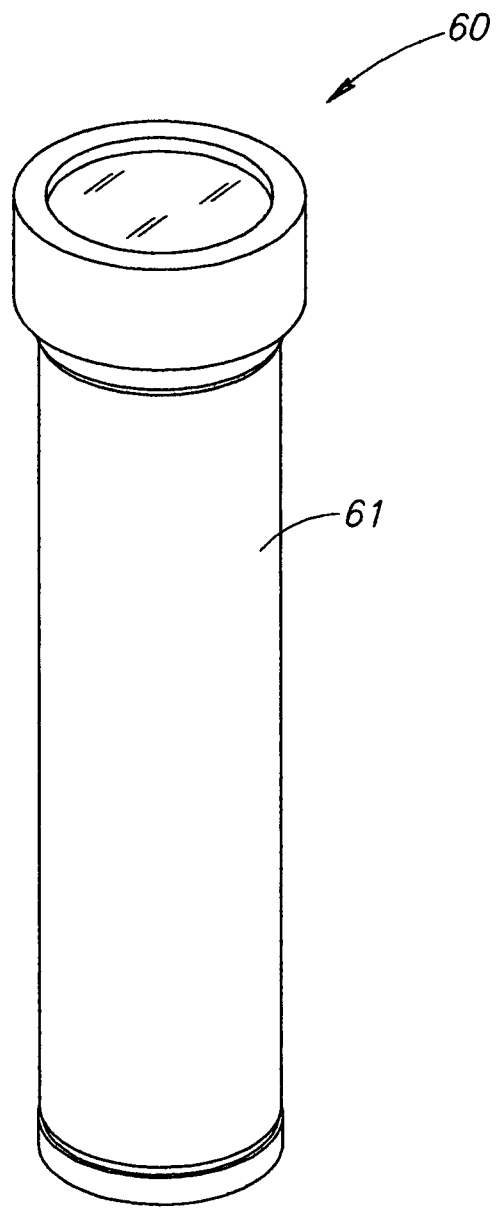
FIG. 4 is a pictorial view of a MR conditional flashlight with a sealed power pack compartment pre-installed with a non-replaceable carbon zinc power pack.
Figures 5, 6:
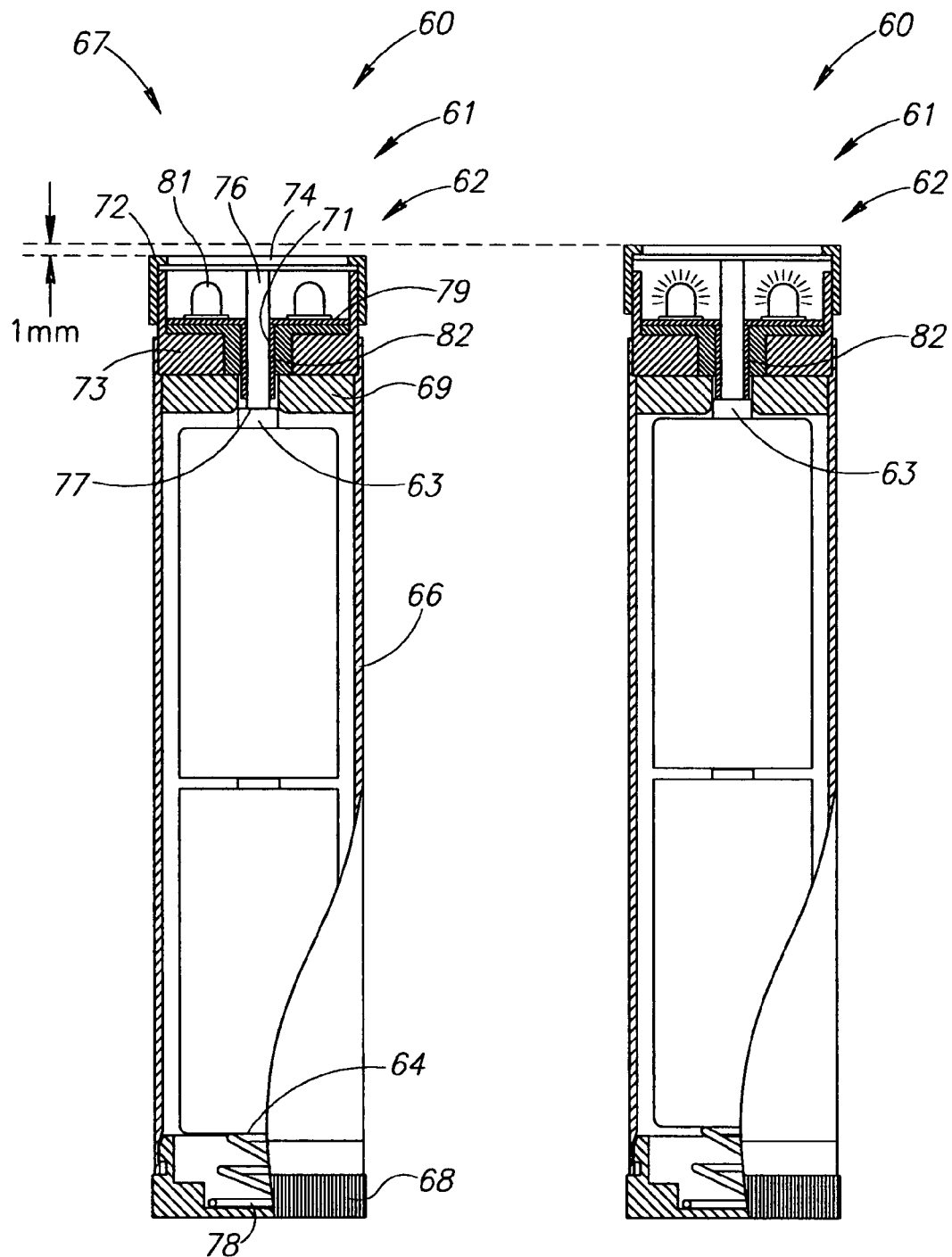
FIG. 5 is a longitudinal cross section of FIG. 4's flashlight in a non-illumination state along line C-C therein.
FIG. 6 is a longitudinal cross section of FIG. 4's flashlight in an illumination state along line C-C therein.

FIGS. 4 to 6 show a disposal MR conditional flashlight 60 having a sealed power pack compartment 61 with a standard mechanical configuration and a standard terminal configuration and pre-installed with a non-replaceable MR conditional carbon zinc power pack 62. The flashlight 60 is intended for disposal after becoming inoperable due to discharge of its carbon zinc power pack 62. The carbon zinc power pack 62 is preferably constituted a pair of AAA, AA, C or D standard 1.5V carbon zinc batteries in series and having an uppermost positive terminal 63 and a lowermost negative terminal 64.

The flashlight 60 includes a MR conditional cylindrical tube 66, a MR conditional flashlight head 67, and a MR conditional flashlight cap 68. The tube 66 is formed from aluminum and has a non-anodized internal surface and an anodized external surface. The tube 66 is fitted with a plastic annular stopper 69 for stopping upward movement of the carbon zinc power pack 62. The annular stopper 69 is formed with a central bore 71 for receiving the positive terminal 63. The flashlight head 67 includes a telescopic arrangement including a leading tubular member 72 and a trailing tubular member 73. The leading tubular member 72 is reciprocal relative to the trailing tubular member 73 along a small stroke of about 1 mm. The leading tubular member 72 includes a transparent front window 74 and a downward depending plastic rod 76 terminating at a lowermost surface 77. The flashlight cap 68 is formed from aluminum and includes a bronze compression spring 78 for positively bearing against the carbon zinc power pack's negative terminal 64 for selectively urging the carbon zinc power pack's positive terminal 63 against the downward depending rod's lowermost surface 77. The trailing tubular member 73 includes an annular plate 79 supporting LEDs 81 in electrical connection with the bronze compression spring 78 and a brass bushing 82 through which the plastic rod 76 slidingly reciprocates therethrough.

FIG. 5 shows the flashlight's OFF position in which the leading tubular member 72 is at its lowermost position relative to the trailing tubular member 73 whereupon the downward depending rod 76 downwardly urges the carbon zinc power pack 62 to break electrical contact between the brass bushing 82 and the positive terminal 63. FIG. 6 shows the flashlight's ON position in which the leading tubular member 72 is at its uppermost position relative to the trailing tubular member 73 whereupon the positive terminal 63 contacts the copper bushing 82 to close the electrical circuit to energize the LEDs 81.

While the invention has been described with respect to a limited number of embodiments, it will be appreciated that many variations, modifications, and other applications of the invention can be made within the scope of the appended claims.

The invention claimed is:

1. Magnetic Resonance (MR) conditional laryngoscope apparatus for use in MR environments, the laryngoscope apparatus comprising
   a MR conditional handheld battery operated laryngoscope which includes an elongate laryngoscope handle and a laryngoscope blade, said handle having a leading handle end adjacent to said laryngoscope blade when connected on said handle, and a trailing handle end, and
   a MR conditional carbon zinc cylindrical power pack for operating said laryngoscope,
   said laryngoscope handle having a cylindrical power pack compartment that has a leading compartment end and a trailing compartment end corresponding with said leading handle end and said trailing handle end, respectively, and a peripheral compartment surface extending between said leading compartment end and said trailing compartment end, and
   said power pack compartment capable of receiving either said power pack or at least one off-the-shelf standard battery, an off-the-shelf standard battery being defined as including a cup-shaped, cylindrical electrically insulated shell, a peripheral surface, and a battery bottom surface in a standard mechanical and terminal configuration such that the standard battery has a positive terminal at a top end and a negative terminal at the battery bottom surface,
   said power pack compartment having a first terminal at said leading compartment end and a second terminal along said peripheral compartment surface in a power pack compartment terminal configuration that is different from the standard mechanical and terminal configuration of the standard battery such that said laryngoscope is inoperable on insertion of said at least one off-the-shelf standard battery in said power pack compartment;
   said cylindrical power pack having non-magnetic properties and including an electrically insulating casing including at least one standard carbon zinc battery which is not rechargeable and each of the at least one standard carbon zinc batteries having a positive terminal,
   said power pack having a leading power pack end with a central opening therein, a trailing power pack end and a cylindrical peripheral power pack surface, and a single positive power pack terminal which comprises a positive terminal of one of the at least one standard carbon zinc batteries positioned at said power pack central opening, and said power pack further comprising a single negative power pack terminal on said peripheral power pack surface, said positive power pack terminal being in a power pack terminal configuration that electrically corresponds to said power pack compartment terminal configuration thereby rendering said laryngoscope operable on insertion of said carbon zinc power pack in said power pack compartment, and
   wherein said power pack casing has a longitudinal axis and said power pack negative terminal is comprised of a resilient elongated flexible member inclined with respect to said casing longitudinal axis and having a free end spaced from said cylindrical peripheral power pack surface in a radial direction for urging toward said longitudinal axis on insertion of said carbon zinc power pack in said power pack compartment of said laryngoscope for ensuring electrical contact with said corresponding power pack compartment's terminal.

2. The MR conditional laryngoscope apparatus according to claim 1 wherein said carbon zinc battery power pack includes at least two standard carbon zinc batteries in series and further comprises a copper plate between an adjacent pair of standard carbon zinc batteries of said at least two standard carbon zinc batteries.

3. A Magnetic Resonance (MR) conditional carbon zinc battery power pack for operating a MR conditional handheld battery operated laryngoscope in MR environments, the laryngoscope having a power pack compartment capable of receiving either said carbon zinc battery power pack or at least one off-the-shelf standard battery, a standard battery being defined as including a cup-shaped, cylindrical electrically insulated shell, a peripheral surface, and a battery bottom surface in a standard mechanical and terminal configuration such that the standard battery has a positive terminal at a top end, and a negative terminal at the battery bottom surface, the laryngoscope power pack compartment having a positive terminal and a negative terminal;
   the carbon zinc battery power pack having non-magnetic properties and comprising an electrically insulating casing that is cylindrical and has a leading power pack end with a central opening therein, a trailing power pack end, and a peripheral external power pack surface enclosing a cavity,
   at least one standard carbon zinc battery, each standard carbon zinc battery having a positive terminal at a top end, inside said battery power pack and oriented with a top end of one of the at least one standard carbon zinc batteries adjacent said power pack leading end, the battery power pack having a single positive power pack terminal which comprises a positive terminal of one of the at least one standard carbon zinc batteries positioned at said battery power pack central opening;
   said battery power pack also having a single negative power pack terminal on said peripheral external power pack surface, said terminal configuration being different from the standard mechanical and terminal configuration of the standard battery,
   thereby rending the laryngoscope operable on insertion of the carbon zinc power pack in the power pack compartment of the laryngoscope and inoperable on insertion of a standard battery in the power pack compartment instead of the carbon zinc power pack;
   and wherein said power pack casing has a longitudinal axis and said negative power pack terminal is comprised of an elongated resilient flexible member inclined with respect to said casing longitudinal axis and having a free end radially spaced apart from said casing cylindrical peripheral surface for urging towards said longitudinal axis on insertion of said carbon zinc battery power pack into the laryngoscope's battery power pack compartment so as to ensure electrical contact with the negative terminal battery power pack compartment.

4. The MR conditional laryngoscope as claimed in claim 1 wherein said laryngoscope handle includes a cylindrical hollow tube, the inside of which is said power pack compartment, said tube being made of aluminum with an anodized internal surface except for a small region on said tube internal surface that is contacted by said elongated flexible member of said negative terminal of said power pack.

5. The MR conditional laryngoscope as claimed in claim 4 wherein said laryngoscope handle tube is electrically insulated and includes an axial directed negative terminal affording the non-standard terminal configuration.

* * * * *